United States Patent
Hishikawa

(10) Patent No.: US 9,889,052 B2
(45) Date of Patent: Feb. 13, 2018

(54) ABSORBENT ARTICLE HAVING TWO OR MORE ABSORBING CORES

(71) Applicants: LIVEDO USA, INC., Wilson, NC (US); LIVEDO CORPORATION, Osaka (JP)

(72) Inventor: Takuya Hishikawa, Wilson, NC (US)

(73) Assignees: LIVEDO USA, INC., Wilson, NC (US); LIVEDO CORPORATION, Osaka (JP)

( * ) Notice: Subject to any disclaimer, the term of this patent is extended or adjusted under 35 U.S.C. 154(b) by 597 days.

(21) Appl. No.: 14/597,647

(22) Filed: Jan. 15, 2015

(65) Prior Publication Data

US 2015/0196436 A1    Jul. 16, 2015

Related U.S. Application Data

(60) Provisional application No. 61/928,177, filed on Jan. 16, 2014.

(51) Int. Cl.
  *A61F 13/539* (2006.01)
  *A61F 13/49* (2006.01)

(52) U.S. Cl.
  CPC ........ *A61F 13/539* (2013.01); *A61F 13/4906* (2013.01)

(58) Field of Classification Search
  CPC ........................................ A61F 13/539; A61F 2013/53908–2013/53991
  See application file for complete search history.

(56) References Cited

U.S. PATENT DOCUMENTS

| 4,623,340 A | * | 11/1986 | Luceri ............... A61F 13/51104 604/370 |
| 4,798,601 A | * | 1/1989 | Shirose ................ A61F 13/515 604/368 |
| 6,068,620 A | * | 5/2000 | Chmielewski .... A61F 13/15658 604/358 |

(Continued)

FOREIGN PATENT DOCUMENTS

| JP | 2006-167196 A | 6/2006 |
| JP | 2007-044124 A | 2/2007 |
| JP | 2009-160242 A | 7/2009 |

*Primary Examiner* — Susan Su
(74) *Attorney, Agent, or Firm* — Westerman, Hattori, Daniels & Adrian, LLP

(57) ABSTRACT

An absorbent article has a lower absorbing core and an upper absorbing core. Each absorbing core includes a liquid-holding material and a liquid-permeable core-wrapping sheet. The liquid-holding material is covered by the liquid-permeable core-wrapping sheet, but it also has an exposed portion not covered by the liquid-permeable core-wrapping sheet. The exposed portions of the lower absorbing core and the upper absorbing core face each other and the liquid-holding materials are connected with each other at the exposed portion. Because the liquid-holding material of the upper absorbing core is in direct contact with the liquid-holding material of the lower absorbing core, the area provides a path through which liquid flows smoothly from the upper absorbing core to the lower absorbing core. Also, because the upper and lower liquid-holding materials are covered by the core-wrapping sheets, deformation of the liquid-holding materials is prevented.

20 Claims, 6 Drawing Sheets

(56) References Cited

U.S. PATENT DOCUMENTS

| | | | |
|---|---|---|---|
| 9,750,651 B2* | 9/2017 | Bianchi | A61F 13/538 |
| 2004/0220539 A1* | 11/2004 | Glaug | A61F 13/537 |
| | | | 604/367 |
| 2007/0179469 A1* | 8/2007 | Takahashi | A61F 13/535 |
| | | | 604/385.101 |
| 2009/0131896 A1* | 5/2009 | Ebitsuka | A61F 13/495 |
| | | | 604/367 |
| 2010/0076392 A1* | 3/2010 | Kudo | A61F 13/4704 |
| | | | 604/385.01 |
| 2010/0312206 A1 | 12/2010 | Fujioka | |
| 2011/0137275 A1* | 6/2011 | Oku | A61F 13/49017 |
| | | | 604/378 |
| 2011/0208147 A1* | 8/2011 | Kawakami | A61F 13/5323 |
| | | | 604/372 |
| 2014/0031776 A1* | 1/2014 | Glaug | A61F 13/53 |
| | | | 604/365 |
| 2014/0163504 A1* | 6/2014 | Bianchi | A61F 13/53717 |
| | | | 604/366 |
| 2015/0351978 A1* | 12/2015 | Langdon | A61F 13/476 |
| | | | 604/385.04 |

* cited by examiner 72    71

ABSORBENT ARTICLE HAVING TWO OR MORE ABSORBING CORES

CROSS-REFERENCE TO RELATED APPLICATION

This non-provisional application claims priority under 35 U.S.C. § 120 on U.S. Provisional Patent Application No. 61/928,177 filed on Jan. 16, 2014, the entire contents of which are hereby incorporated by reference.

TECHNICAL FIELD

The present invention related to an absorbent article of liquid, more particularly, absorbent articles used, for example, as urine pads, and inner pads for pull-on-type diapers and tape-on-briefs-type diapers.

BACKGROUND

Among common absorbent articles such as urine pads, pull-on-type diapers, and tape-on-briefs-type diapers, absorbent articles including a plurality of absorbers stacked in the thickness direction have been devised in an attempt to increase the amount of urine absorbed while minimizing leakage of urine.

In particular, pull-on-type diapers, which are often used by wearers who can walk, may have problems such as twisting and deformation of absorbing cores stacked in the thickness direction during wearing.

As disclosed in Japanese Patent Application Publications Nos. 2009-160242 and 2007-44124, a technique has so far been developed and used in which absorbing cores including a liquid-holding material covered on the top surface, side surfaces, and both sides of the bottom surface, or in its entirety, with a non-woven cloth are stacked in the thickness direction and are bonded together with an adhesive to prevent deformation due to twisting of the absorbing cores and to increase the absorption rate.

However, when the entire liquid-holding material is covered with a non-woven cloth formed of a synthetic fiber, a hydrophilic agent needs to be applied to the non-woven cloth so that it has hydrophilic properties. The hydrophilic agent, however, may be washed away after permeation of urine multiple times, and accordingly the non-woven cloth may lose its hydrophilic properties. It has been reported that, after urination in small amounts multiple times, urine is repelled by the non-woven cloth covering the absorber and leaks from the side surfaces of the absorbing core along the surface of the non-woven cloth.

As disclosed in Japanese Patent Application Publication No. 2006-167196, an attempt has been made to provide a second sheet between an upper absorbing core cut in a U-shape and a lower absorbing core at the central position in the width direction of the absorbing cores for improved diffusibility, which is intended to reduce wetback by effectively utilizing the absorbing cores. However, because of the property of absorbing urine over a wide area of the second sheet, some urine remains on the second sheet after urination multiple times, which makes it difficult to improve the absorption rate.

SUMMARY

Generally, there is a need for an absorbent article that maintains its absorption capacity and absorption rate after urination multiple times. At the same time, it is desirable to develop an absorbent article that supports urination of multiple times while maintaining its strength against twisting and deformation of an absorber due to the motion of the wearer.

The absorbing article of the present invention includes a lower absorbing core and an upper absorbing core. The lower absorbing core includes a liquid-permeable core-wrapping sheet and a liquid-holding material including such as cellulose fibers. The lower liquid-holding material is covered by the liquid-permeable core-wrapping sheet at least on the lower side, and on the right and left sides. The lower liquid-holding material has an exposed portion not covered by the liquid-permeable core-wrapping sheet on the side facing the upper absorbing core.

Like the lower absorbing core, the upper absorbing core also includes a liquid-permeable core-wrapping sheet and a liquid-holding material including, for example, cellulose fibers. In the upper absorbing core, the liquid-holding material is covered by the liquid-permeable upper core-wrapping sheet at least on the upper side, and on the right and left sides. The liquid-holding material has an exposed portion not covered by the liquid-permeable upper core-wrapping sheet on the side facing the lower absorbing core.

The liquid-holding material in the lower absorbing core and the liquid-holding material in the upper absorbing core are connected with each other at a connecting area where the exposed portions face each other. The connecting area can be positioned at a central portion with respect to the width direction of the absorbing core. The liquid-permeable lower core-wrapping sheet can include hydrophilic long-fibered non-woven cloth. The liquid-permeable lower core-wrapping sheet can be formed of a single sheet.

The liquid-holding material of the lower absorbing core (hereinafter "lower liquid-holding material"; other portions are also referred to similarly) can have various shape depending on the use of the absorbent article, such as a rectangular shape, and a hourglass shape. In the hourglass shape, a width of the central portion with respect to the longitudinal direction is smaller than a width at the end portion with respect to the longitudinal direction of the lower absorbing core.

The maximum width of the lower liquid-holding material can be greater than the maximum width of the upper liquid-holding material, and the minimum width of the lower liquid-holding material can be equal to, or greater than, the minimum width of the upper liquid-holding material. The lower absorbing core and the upper absorbing core can be partially bonded by an adhesive such as hot-melt adhesive.

The lower liquid-holding material can further contain liquid-absorbing polymer mixed with the cellulose fibers. The liquid-absorbing polymer can preferably be uniformly distributed in cellulose fibers.

The absorbent article can be used as an inner pad attached to a crotch portion of a pull-on-type diaper exterior sheet.

The absorbent article can have elasticized flaps on both sides with respect to the width direction such that liquid leakage is prevented by the stretchy flaps. The elasticized flaps are attached on the upper side of the absorbent article. The elasticized flaps can preferably be attached to the top sheet.

The absorbent article can further include: a liquid-permeable top sheet and a liquid-impermeable back sheet. The absorbing core can be disposed between the top sheet and the back sheet.

Figure 1:
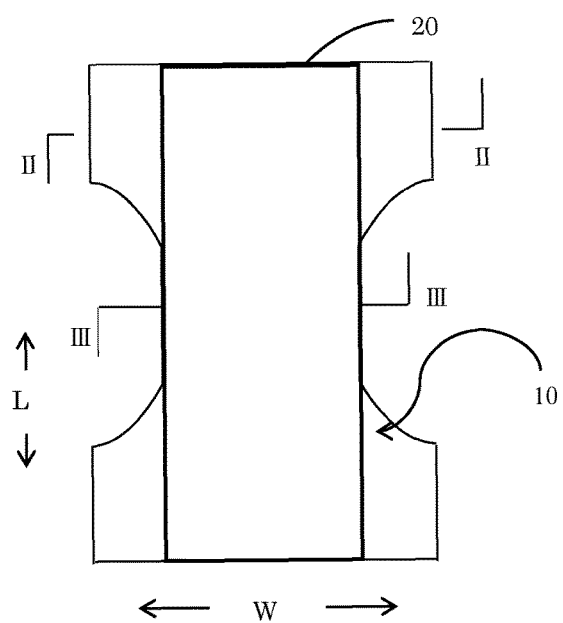
FIG. 1 illustrates an example of the absorbent article of the present invention as viewed from the side facing the top sheet.

L: longitudinal direction
W: width direction
10: lower absorbing core
11: lower liquid-holding material
12: lower core-wrapping sheet
20: upper absorbing core
21: upper liquid-holding material
22: upper core-wrapping sheet
30: absorbing core assembly
31: connecting area
32: adhesive
50: pull-on-type diaper
51: exterior cover
52: leg opening
53: inner pad
54: top sheet
55: back sheet
56: adhesive
57: flap
58: flap elastic member
63: front portion
64: back portion
65: joined portion
66: belly portion
67: waistline area
69: exterior cover elastic member
71: adhesive ejecting nozzle
72: hot-air nozzles

DETAILED EXPLANATION

An absorbent article of the present invention is now described with reference to FIGS. 1 to 10.

FIG. 1 illustrates an example of the absorbent article of the present invention as viewed from the upper side. The absorbent article includes a lower absorbing core 10 and an upper absorbing core 20. The absorbent article can have any geometrical shape depending on the use. In this example, the lower absorbing core 10 has an hourglass shape that is narrower at the central portion of the absorbing core and that is wider toward both ends in the longitudinal direction, and the upper absorbing core 20 has a rectangular shape. The upper absorbing core 20 preferably has a width smaller than or equal to the minimum width of the lower absorbing core 10 at the central portion in the longitudinal direction.

Figure 2:
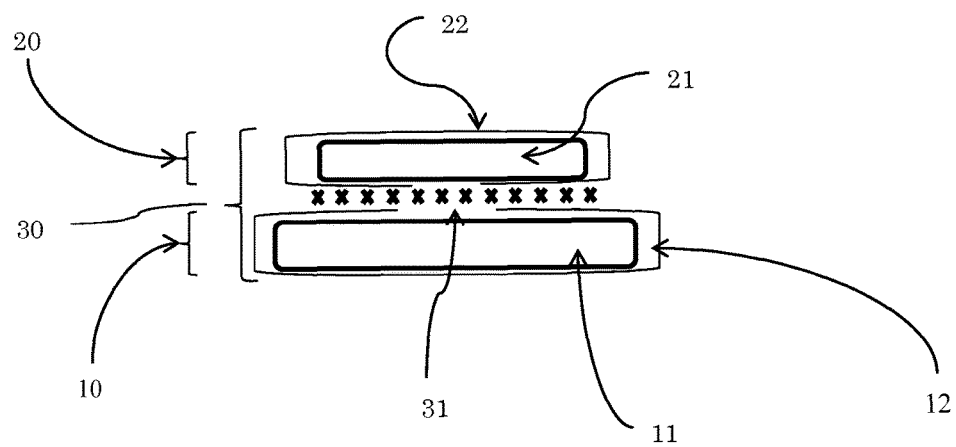
FIG. 2 is a sectional view taken along line II-II near one end in FIG. 1.

FIG. 2 is a sectional view taken along line II-II in FIG. 1 near one end. FIG. 3 is a sectional view taken along line III-III near the central portion in the longitudinal direction.

The lower absorbing core 10 includes a lower liquid-holding material 11 and a liquid-permeable lower core-wrapping sheet 12 which is wrapping the lower liquid-holding material 11. The lower liquid-holding material 11 is made of material which absorbs and holds liquid therein, such as cellulose fibers. The liquid-permeable lower core-wrapping sheet 12 covers the lower liquid-holding material 11 at least on the lower side, and on right and left sides, but the lower liquid-holding material has an exposed portion not covered by the liquid-permeable lower core-wrapping sheet 12 on a side facing the upper absorbing core 20.

The upper absorbing core 20 similarly has a liquid-permeable upper core-wrapping sheet 22 and an upper liquid-holding material 21. The upper liquid-holding material 21 is made of material which can absorb and hold liquid therein, such as cellulose fibers. The upper core-wrapping sheet 22 covers the upper liquid-holding material 21 at least on the upper side, and on right and left sides, but the upper liquid-holding material 21 has an exposed portion not covered by the upper core-wrapping sheet 22 on a side facing the lower absorbing core 10.

The exposed portion of the lower liquid-holding material 11 and the exposed portion of the upper liquid-holding material 21 face each other, and they form a connecting area 31. The connecting area 31 can be positioned at a central portion with respect to the width direction W of the lower absorbing core 10 and the upper absorbing core 20. The liquid-permeable lower core-wrapping sheet 12 can be made of hydrophilic long-fibered non-woven cloth. The liquid-permeable lower core-wrapping sheet can be formed of a single sheet.

The lower liquid-holding material 11 can have a hourglass shape where a width of the central portion with respect to the longitudinal direction which is smaller than a width at the end portion with respect to the longitudinal direction of the lower absorbing core. The maximum width of the lower liquid-holding material can be greater than the maximum width of the upper liquid-holding material, and the minimum width of the lower liquid-holding material can be equal to, or greater than, the minimum width of the upper liquid-holding material. The lower absorbing core 10 and the upper absorbing core 20 can be partially bonded by an adhesive such as hot-melt adhesive.

The liquid-holding material 11 of the lower absorbing core 10 can contain a liquid-absorbing polymer mixed with the cellulose fibers such that urine drawn by the cellulose fibers upon urination can be retained by the liquid-absorbing polymer, thus minimizing wetback under the pressure applied by the body surface.

Preferably, liquid-absorbing polymer particles are uniformly distributed in the cellulose fibers in the lower absorbing core 10. The uniform distribution prevents the phenomenon in which absorption of urine is blocked by gel blocking, which occurs when extremely concentrated liquid-absorbing polymer absorb urine and adhere to each other in a gelled state.

The absorbent article can be an inner pad attached to a crotch portion of a pull-on-type diaper exterior sheet. The absorbent article can have elasticized flaps on both sides with respect to the width direction of the top sheet such that liquid leakage is prevented by the stretchy flaps.

Figure 3A:
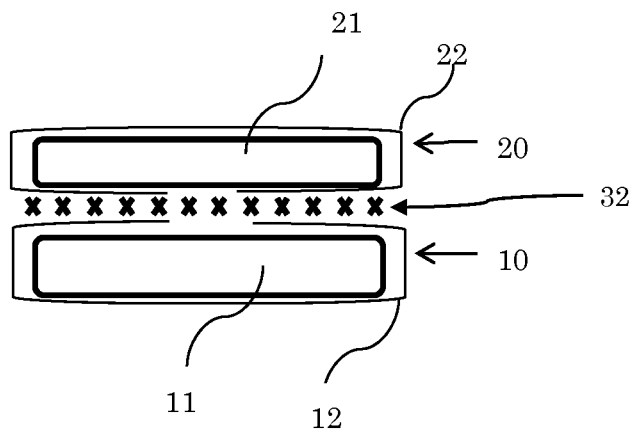
FIG. 3A is a sectional view taken along line III-III near the central portion in the longitudinal direction in FIG. 1.
Figure 3B:
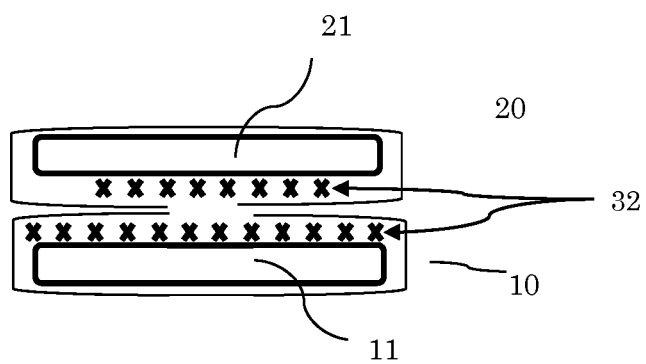
FIG. 3B is another example of sectional view taken along line III-III near the central portion in the longitudinal direction in FIG. 1.

The lower absorbing core 10 and the upper absorbing core 20 can be bonded together at the exposed portions with an adhesive 32 such as a hot-melt adhesive, which forms a connecting area 31 where the lower liquid-holding material 11 and the upper liquid-holding material 21 are bonded together. This prevents deformation and twisting due to displacement of the upper and lower absorbing cores 10, 20. When the bonding also can be formed between the core-wrapping sheets, as shown in FIG. 3A and FIG. 3B, which ensures sufficient bond strength between the upper and lower absorbing cores even if urine breaks the joint between the liquid-holding materials 11, 21. Also, the adhesive 32 can be applied between the upper liquid-holding material 21 and the upper core-wrapping sheet 22 and between the lower liquid-holding material 11 and the lower core-wrapping sheet 12.

According to the present invention, the absorbent article has an area where the upper liquid-holding material of the upper absorbing core 20 is in direct contact with the lower liquid-holding material of the lower absorbing core 10. The connecting area 31 provides a path through which liquid, such as urine, flows smoothly from the upper absorbing core 20 to the lower absorbing core 10. The connecting area 31 can be located at the substantially central portion with respect to the width direction W of the absorbent article. This arrangement allows a smooth flow of liquid in the central region, where more liquid can be received.

The core wrapping sheet 12 can be made of a non-woven cloth. Because the core wrapping sheet 12 is hydrophilic, if a large amount of urine is excreted at a time, and the urine is too much to be immediately absorbed by the upper absorbing core, the urine can also be absorbed through the side surfaces of the core wrapping sheet 12. Also, because the upper and lower liquid-holding materials 11, 21 are covered by the core-wrapping sheets 12, 22, deformation of the liquid-holding materials is prevented.

A long-fibered non-woven cloth can be made hydrophilic by coating the surface with a hydrophilic agent during the manufacture. On the other hand, when a short-fibered non-woven cloth is made hydrophilic, fiber web is often mixed with a hydrophilic agent during the manufacture. The hydrophilic agent coating the long-fibered non-woven cloth can come off more easily than the hydrophilic agent mixed in the short-fibered non-woven cloth.

If the lower core-wrapping sheet 12 is made of the hydrophilic long-fibered non-woven cloth, when urine reaches the lower absorbing core 10 after multiple times of urination, the urine flows through the lower core-wrapping sheet 12 and it can wash the hydrophilic agent away from the long-fibered non-woven cloth, so that the lower core-wrapping sheet 12 becomes less hydrophilic or nearly water-repellent. The lower core-wrapping sheet 12, which has become nearly water-repellent, reduces wetback to the body surface when the lower absorbing core 10 in a diaper is pressed by the pressure of the body.

Upon further urination, the urine can be absorbed through the connecting area 31, and the urine can be still retained by the lower liquid-holding material 11. This reduces wetback, i.e., a flow of urine retained by the lower liquid-holding material 11 back into the upper liquid-holding material 21, without blocking absorption of urine into the lower liquid-holding material 11, thus improving the comfort of the wearer.

When the lower core-wrapping sheet 12 is formed of a single sheet, deformation of the absorbing core, due to absorption of urine and the motion of the wearer, can be effectively prevented.

Figure 4:
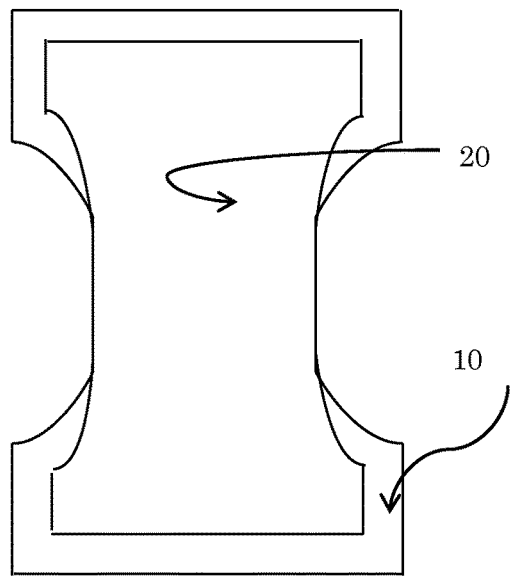
FIG. 4 illustrates another example of the shape of the absorbent article of the present invention.

FIG. 4 shows another example of the absorbent article of the present invention, which is of a modification of the shape of the absorbing cores. Whereas the upper absorbing core 20 in FIG. 1 has a rectangular shape with a uniform width in the longitudinal direction, the upper absorbing core 20 in FIG. 4 has an hourglass shape that is similar to that of the lower absorbing core 10. The upper absorbing core 20 preferably has a width smaller than or equal to the minimum width of the lower absorbing core 10 at the central portion in the longitudinal direction.

When the upper absorbing core 20 has an hourglass shape that is wider in the portions corresponding to the abdomen and back, it can cover a wide area of the front and back of the crotch while reducing its rigid feel. This allows urine to be absorbed without leaking along the body surface of the wearer in the longitudinal direction.

Also, when the maximum width of the lower absorbing core 10 is greater than the maximum width of the upper absorbing core 20, more urine can be retained by the lower absorbing core 10. In addition, if the minimum width of the lower absorbing core 10 is equal to or greater than the minimum width of the upper absorbing core 20, urine can be absorbed without leaking outside the core-wrapping sheet of the lower absorbing core 10 wherever urination occurs on the surface of the upper absorbing core 20.

The liquid-holding material of the absorbing core can be any material suitable for the purpose. An example of preferable material is a mixture of cellulose fibers and absorbent polymer particles. The mixing ratio of the cellulose fiber and absorbent polymer particles can be the same or different between the upper liquid-holding material and the lower liquid-holding material. Thermoplastic adhesive also can be added. Liquid absorbent polymer absorbs and holds the liquid. Liquid absorbent polymer is commonly made from acrylic acid, but other materials can be also used. Liquid absorbent polymer particles are preferably contained in the absorbing core in the range of 10 to 65 wt % of the liquid-holding material.

The core wrapping sheet can be made of a liquid permeable non-woven cloth. The examples are spun-bonded non-woven cloth made hydrophilic. Other non-woven cloths such as SMS, air through also can be used. The material can be the same or different between the upper core wrapping sheet and the lower core wrapping sheet. The upper core wrapping sheet can preferably made of tissue paper. The lower core wrapping sheet can be preferably made of long-fibered non-woven cloth which is made liquid permeable and hydrophilic.

When the lower core wrapping sheet is made liquid permeable and hydrophilic, it can be preferable to use a hydrophilic-making agent which tends to be easily washed away by the liquid so as to make the core wrapping sheet less liquid permeable. The decrease in liquid permeability can reduce wetback (wetback is a flow of liquid such as urine retained by the liquid-holding material back out of the liquid-holding material). The amount of hydrophilicity can be the same or different between the upper core wrapping sheet and the lower core wrapping sheet.

The exterior cover can be made of any material which feels comfortable and which has air permeability and flexibility. Examples of preferable materials are cellulose, rayon, acetate, polyethylene, polypropylene, nylon, polyester, acrylic fiber. Liquid impermeable material is preferable.

Polypropylene has advantages in strength, flexibility, and material cost. Non-woven cloth made of mixed resin of polyethylene and polypropylene, or mixed resin of polyethylene and polyethylene terephthalate can be used for the exterior cover. The non-woven cloth can be made by a process such as spun-bonding, SMS, SMMS, or point bonding. The material is preferably fusible so that the side portions can be bonded by heat.

Elastic material such as elastic thread can be made of polyurethane, natural rubber, etc., which are widely used in disposable absorbent articles. Also, the elastic material can be a polyurethane film ribbon.

The adhesive preferably is liquid non-soluble and maintains adhesive power after getting wet. A hot-melt adhesive can be typically used and suitable one can be chosen from various kinds such as olefin series, rubber series, and rubber olefin series.

The top sheet can be made of a woven or non-woven cloth of liquid permeable synthetic fabric. The synthetic fabric can be hydrophilic fabric selected from rayon, pulp, etc. The material for the top sheet can be a material similar to that of the outer cover sheet. The top sheet should be liquid permeable and harmless to the human body. The examples are fabric of cellulose, rayon, acetate, polyethylene, polypropylene, nylon, polyester, acrylic. Preferable materials are spun bonded non-woven cloth and other non-woven cloths, such as air-through, and air-laid, also can be used. It is preferable that the top sheet feels comfortable and soft and has good durability.

The back sheet should be a liquid impermeable sheet to prevent the liquid from leaking on the side opposite from the human body. On the other hand, the back sheet can be either vapor permeable or impermeable. When the back sheet is vapor permeable, humidity is reduced on the side of human body.

The examples of materials for the back sheet are synthetic resin film, water shedding non-woven cloth, moisture vapor permeable film, and combination with other sheets.

The absorbent article of the present invention can be used in a pull-on-type diaper, and it will provides a comfortable thin absorbent article that is less likely to cause leakage of urine or to give a wet feeling to wearers who move actively.

Pull-on-type diapers are generally worn by persons who are capable of walking, and they are also capable of putting on and taking off the diapers by themselves, and they can control their urination to some extent by themselves. The use of the absorbent article in a pull-on-type diaper provides resistance to deformation of the liquid-holding material and wetback after small-amounts multiple-time urinations when used by active users.

Figure 5:
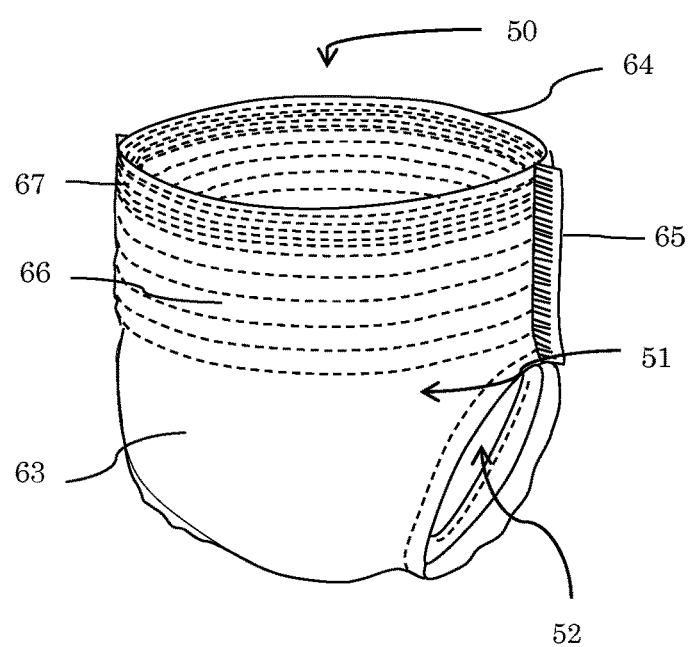
FIG. 5 is a perspective view of an exterior cover of a pull-on-type diaper in which the absorbent article of the present invention can be used as an inner pad.
Figure 6:
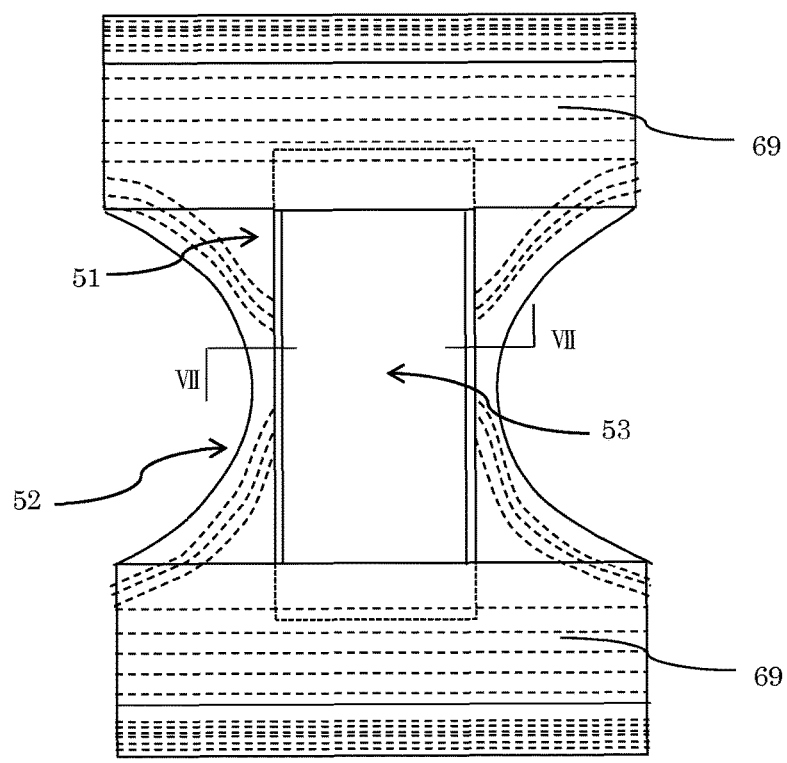
FIG. 6 is a development view of a first pull-on-type diaper.
Figure 7:
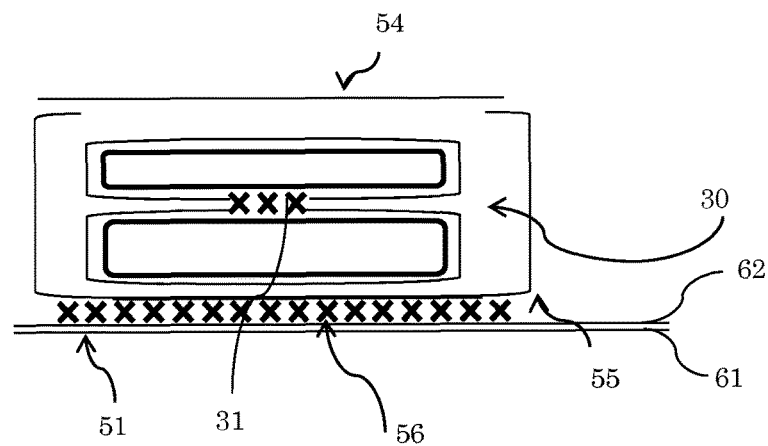
FIG. 7 is a sectional view of the first pull-on-type diaper taken along line VII-VII in FIG. 6.

FIGS. 5 to 7 illustrate another embodiment of the present invention. FIG. 5 is an illustration of an exterior cover 51 of a pull-on-type diaper 50. In this embodiment, the absorbent article is used as an inner pad 53 attached to a crotch portion inside of the exterior cover 51 of the pull-on-type diaper 50.

As shown in FIG. 5, the exterior cover 51 has a pair of leg openings 52. The front portion 63 and the back portion 64 can be joined at joined portions 65 above the upper side of the leg openings 52, and the joined portions are positioned at the right and left sides of the wearer's body.

FIG. 6 shows a development view of the pull-on-type diaper 50. FIG. 7 is a sectional view of an inner pad 53 taken along line VII-VII in FIG. 6. The absorbent article described above is disposed as an inner pad 53 between a pair of leg openings 52 in an exterior cover 51 of the pull-on-type diaper 50 (FIG. 6). As shown in FIG. 7, the absorbent article can have a liquid-permeable top sheet 54. The absorbent article (inner pad) 53 also is covered by a liquid-impermeable back sheet 55. The back sheet 55 of the absorbent article 53 is preferably bonded to the exterior cover 51 with an adhesive 56 such as a hot-melt adhesive.

Exterior cover elastic members 69 can be attached at the leg portion, the belly portion 66, and waistline area 67 of the exterior cover 51. Also, the suitable elasticity can be chosen for the elastic member 69 of each portion. The elastic member 69 makes the exterior cover 51 fit the wearer's body, and prevents leakage from around the leg or front or back portion when the wearer moves.

When the inner pad 53 is attached to the exterior cover 51, an adhesive 56 can be applied onto either the back sheet 55 of the inner pad 53 or the exterior cover 51 by various processes such as coater process, curtain process, bead process. The need not be bonded to the exterior cover 51 over the entire length as long as sufficient adhesion is obtained.

When inner pad 53 is not bonded 53 to the exterior cover 51 over the entire length, the end portions of the inner pad 53 can stand up causing a discomfort to the wearer. Therefore, some measure may be taken to prevent it, for example, non-woven cloth or film can be overlaid on the body side at the end portions in the longitudinal direction, as shown in FIG. 6.

The waistline area 67 preferably has elasticity such that it fits the wearer's body. For example, a ribbon elastic sheet or elastic threads can be placed at the waistline area 67. Also, the exterior cover 51 can be made longer than the inner pad 53, and elastic materials can be placed making the elastic portion at the portion where the inner pad 53 does not overlie the exterior cover 51. The elastic portion can be folded down toward the inner pad 53.

The liquid-holding material 11, 21 is preferably wrapped by a core-wrapping sheet 12, 22 such as tissue paper or non-woven cloth except the bonded area. The core-wrapping sheet 12, 22 facing the liquid-holding material 11, 21 can be bonded with the liquid-holding material 11 with an adhesive in order to prevent the absorbing core 10, 20 from losing shape.

The lower liquid-holding material 11 is preferably covered with a non-woven cloth. It is preferable that the agent making the lower core-wrapping sheet 12 hydrophilic tends to be easily washed away by the liquid and making the core wrapping sheet become less liquid permeable or nearly liquid repellant.

This can be achieved by applying a hydrophilic-making agent onto a water-repellent long-fibered non-woven cloth. Also, non-woven cloth can be manufactured from the fabric mixed with a water-soluble hydrophilic making agent.

The core-wrapping sheet 12, 22 facing the liquid-holding material 11,21 can be bonded with the liquid-holding material with an adhesive in order to prevent the absorbing core 10,20 from losing shape, and also to prevent misalignment of the upper liquid-holding material 21 and the lower liquid-holding material 11. The adhesive should be applied with sufficient spaces such that the water penetration is not hindered from the upper liquid-holding material 21 to the lower liquid-holding material 11. The adhesive preferably should be harmless to human body. The bonded area need not extend over the whole surface.

Figure 8:
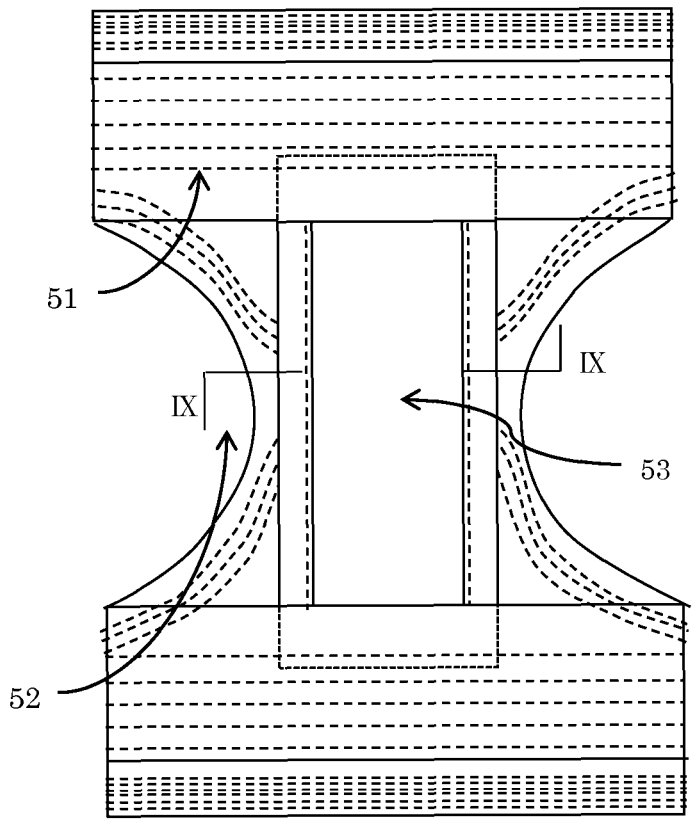
FIG. 8 is a development view of a second example of the pull-on-type diaper.
Figure 9:
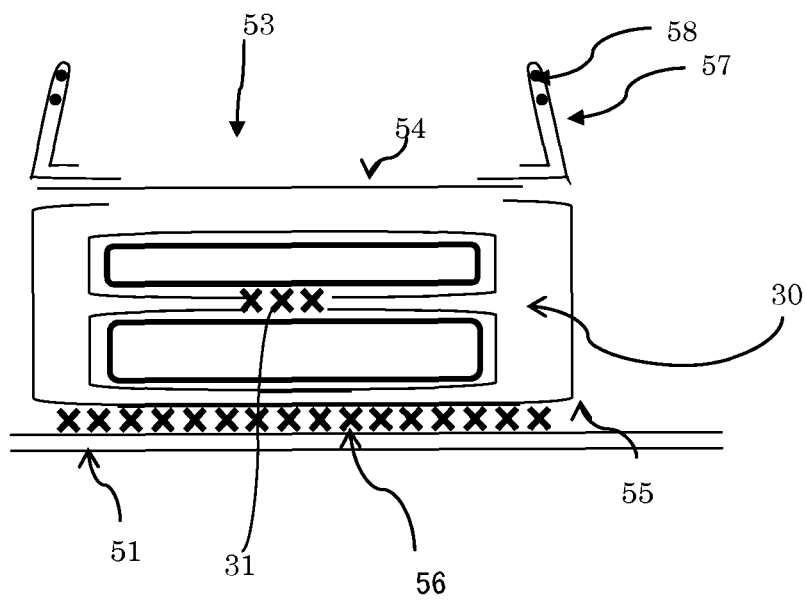
FIG. 9 is a sectional view of the second example of the pull-on-type diaper taken along line IX-IX in FIG. 8.

FIGS. 8 to 9 illustrate another embodiment of the present invention. As shown in FIGS. 8 and 9, the absorbent article 53 can have flaps 57 on both sides with respect to the width direction of the top sheet 54 such that liquid leakage from the leg opening 52 is prevented by the flaps 57. The flaps 57 can be either elasticized or non-elasticized.

When a great amount of urine is discharged at a time, there may be some urine which is not immediately absorbed into the absorbing core assembly 30, and it can leak from the leg openings 52. The flaps 57 is formed to stand up vertically with respect to the inner pad surface when the wearer wears the diaper and the flaps 57 block the urine from flowing sideward and hold the urine inside between the flaps 57 until the liquid absorbent polymer particles absorb the urine. The flaps 57 can have elastic members 58, preferably at the top of the flaps 57 so as to keep the flaps standing toward the wearer's body surface. The flaps can be made of a liquid impermeable sheet.

The lower absorbing core 10 and the upper absorbing core 20 can be bonded by an adhesive such as hot-melt adhesive. Also, the liquid-holding material and core wrapping sheet can be bonded by adhesive. The two surfaces are partially bonded such that displacement of the two surfaces is prevented while sufficient portions of the surfaces which are not covered by the adhesive is left and liquid can transfer between the two surfaces. The adhesive can be preferably a hot-melt adhesive.

The adhesive can be applied on either the liquid holding materials, the core wrapping sheets, or the both by any method, such as a curtain method, a spiral method, a coating method and a bead/dot method.

In the curtain method, the adhesive is sprayed such that the droplets of the adhesive are scattered on the sheet.

Figure 10A:
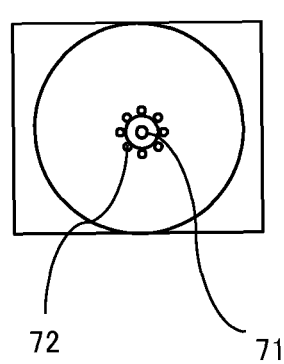
FIGS. 10A to 10C illustrate a method of distributing adhesive in a loop shape on a core-wrapping sheet or a liquid-holding material.
Figure 10B:
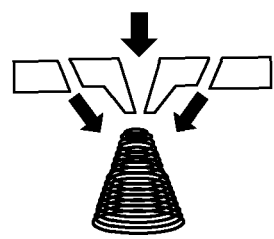
Figure 10C:
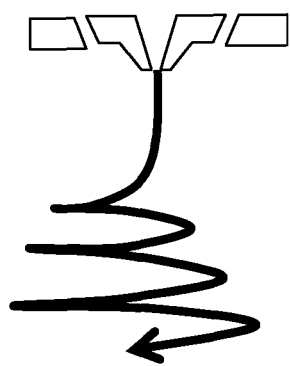

In a spiral method shown by FIGS. 10A to 10C, an adhesive ejecting nozzle 71 is surrounded by a number of hot-air nozzles 72. As shown by FIGS. 10B and 10C, the adhesive ejected from the adhesive-ejecting nozzle is blown by the hot air sequentially ejected from the hot-air nozzles 72 in a rotational order such that the adhesive is spirally applied on to the sheet moving under the nozzle.

In the coating method, the adhesive is simply applied on the sheet with a thickness. Therefore, in order to partially bond the surfaces, the adhesive should be applied in a pattern. In the bead/dot method, the adhesive is applied on the sheet in a thin line or dotted line. These methods are examples of applying the adhesive, and a person of ordinary skill in the art can employ any method for the application of adhesive.

What is claimed is:

1. An absorbent article, comprising:
    a lower absorbing core comprising a lower liquid-holding material and a lower liquid-permeable core-wrapping sheet; and
    an upper absorbing core comprising an upper liquid-holding material and an upper liquid-permeable core-wrapping sheet,
    wherein the lower liquid-holding material is covered by the liquid-permeable lower core-wrapping sheet at least on a lower side, and on right and left sides, the lower liquid-holding material having a first exposed portion not covered by the liquid-permeable lower core-wrapping sheet on a side facing the upper absorbing core,
    wherein the upper liquid-holding material is covered by the liquid-permeable upper core-wrapping sheet at least on an upper side, and on right and left sides, the upper liquid-holding material having a second exposed portion not covered by the liquid-permeable upper core-wrapping sheet on a side facing the lower absorbing core;
    wherein the upper liquid-holding material and the lower liquid-holding material are connected directly with each other at a connecting area where the first exposed portion and the second exposed portion face each other.

2. The absorbent article according to claim 1, wherein the connecting area is positioned at a central portion with respect to the width direction of the absorbing core.

3. The absorbent article according to claim 1, wherein the liquid-permeable lower core-wrapping sheet comprises hydrophilic long-fibered non-woven cloth.

4. The absorbent article according to claim 1, wherein at least one of the liquid-permeable lower core-wrapping sheet or the liquid-permeable upper core-wrapping sheet is formed of a single piece of sheet.

5. The absorbent article according to claim 1, wherein the upper absorbing core has a rectangular shape.

6. The absorbent article according to claim 1, wherein the lower absorbing core has a rectangular shape.

7. The absorbent article according to claim 1, wherein the lower absorbing material has an hourglass shape where a first width of the central portion with respect to the longitudinal direction is smaller than a second width at the end portion with respect to the longitudinal direction of the lower absorbing material.

8. The absorbent article according to claim 1, wherein a first maximum width of the lower absorbing material is greater than a second maximum width of the upper absorbing material, and a first minimum width of the lower absorbing material is equal to, or greater than, a second minimum width of the upper absorbing material.

9. The absorbent article according to claim 1, wherein the lower absorbing core and the upper absorbing core are partially bonded by a hot-melt adhesive.

10. The absorbent article according to claim 1, wherein the lower liquid-holding material and the upper liquid-holding material comprise cellulose fibers.

11. The absorbent article according to claim 10, wherein the lower liquid-holding material and the upper liquid-holding material further comprise liquid-absorbing polymer particles mixed with the cellulose fibers.

12. The absorbent article according to claim 11, wherein the liquid-absorbing polymer particles are uniformly distributed in the cellulose fibers.

13. The absorbent article according to claim 1, wherein the lower liquid-holding material and the upper liquid-holding material comprise liquid-absorbing polymer particles.

14. The absorbent article according to claim 1, further comprising a liquid-permeable top sheet over the upper absorbing core.

15. The absorbent article according to claim 1, further comprising elasticized flaps on both sides with respect to the width direction of the top sheet such that liquid leakage is prevented by the elasticized flaps.

16. The absorbent article according to claim 15, wherein the elasticized flaps are attached to the liquid-permeable top sheet.

17. The absorbent article according to claim 1, wherein the absorbent article comprises no flaps.

18. The absorbent article according to claim 1, further comprising a liquid-impermeable back sheet under the lower absorbing core.

19. The absorbent article according to claim 18, wherein the liquid-impermeable back sheet extends and covers side portions of the lower absorbing core and the upper absorbing core.

20. The absorbent article according to claim 1, wherein the absorbent article is a diaper, the absorbent article further comprises a pull-on shaped exterior sheet, and the lower absorbing core being placed inside of the diaper exterior sheet.

* * * * *